United States Patent [19]

Berger

[11] Patent Number: 5,423,850
[45] Date of Patent: Jun. 13, 1995

[54] BALLOON COMPRESSOR FOR INTERNAL FIXATION OF BONE FRACTURES

[76] Inventor: J. Lee Berger, 895 Mohawk Rd., Franklin Lakes, N.J. 07417

[21] Appl. No.: 153,030

[22] Filed: Nov. 17, 1993

Related U.S. Application Data

[63] Continuation-in-part of Ser. No. 130,434, Oct. 1, 1993.

[51] Int. Cl.⁶ ............................................. A61B 17/18
[52] U.S. Cl. ........................................ 606/192; 604/96
[58] Field of Search .............. 606/191, 192, 194, 195, 606/60–62; 604/95–104, 164; 128/DIG. 20

[56] References Cited

U.S. PATENT DOCUMENTS

| | | |
|---|---|---|
| 3,760,802 | 9/1973 | Fischer et al. . |
| 3,779,239 | 12/1983 | Fischer et al. . |
| 4,227,518 | 10/1980 | Aginsky . |
| 4,275,717 | 6/1981 | Bolesky . |
| 4,313,434 | 2/1982 | Segar . |
| 4,457,301 | 7/1984 | Walker . |
| 4,467,794 | 8/1984 | Maffei et al. . |
| 4,946,459 | 8/1990 | Bradshaw et al. . |
| 5,002,543 | 3/1991 | Bradshaw et al. . |
| 5,034,013 | 7/1991 | Kyle et al. . |
| 5,104,399 | 4/1992 | Lazaros ............................... 606/153 |
| 5,108,404 | 4/1992 | Schocten et al. ..................... 606/60 |
| 5,263,931 | 11/1953 | Miller .................................. 606/192 |

Primary Examiner—Stephen C. Pellegrino
Assistant Examiner—William W. Lewis
Attorney, Agent, or Firm—Gipple & Hale

[57] ABSTRACT

The present invention is directed toward a method for performing an internal fixation of fractures of tubular bones using a balloon catheter fixation device which is guided and transported through the medullary canal and fracture site of the bone by a plurality of guide wires mounted in said balloon catheter fixation device and once placed in position in the bone inflated inside the bone and tightened by applying pressure on the catheter outside of the bone to apply a compression force across the fracture site enhancing the stability of the fractured bone and promoting osseous healing.

20 Claims, 1 Drawing Sheet

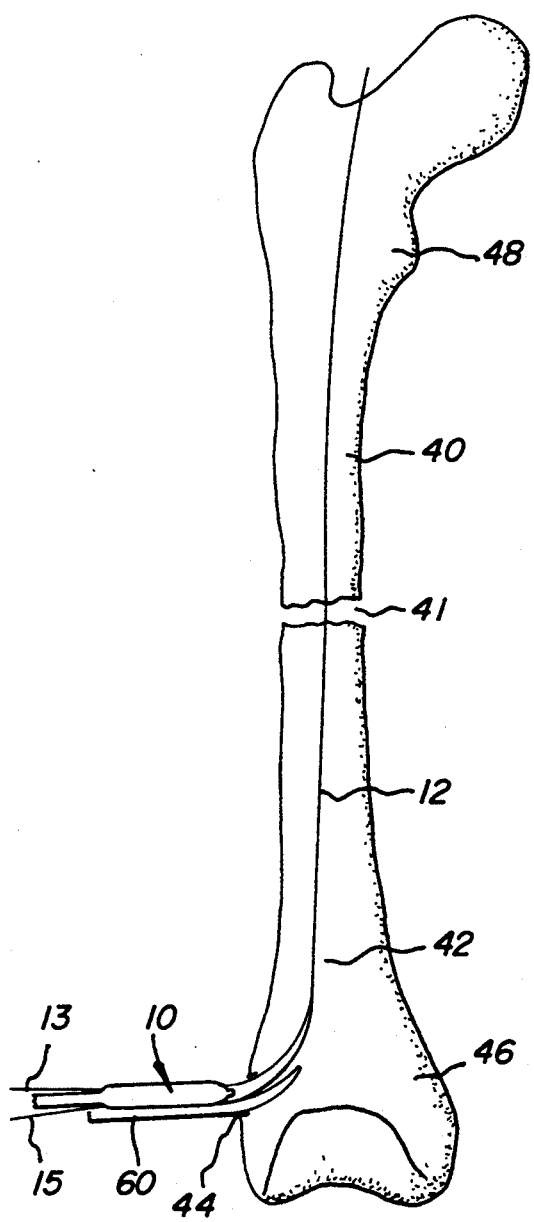
Fig. 1
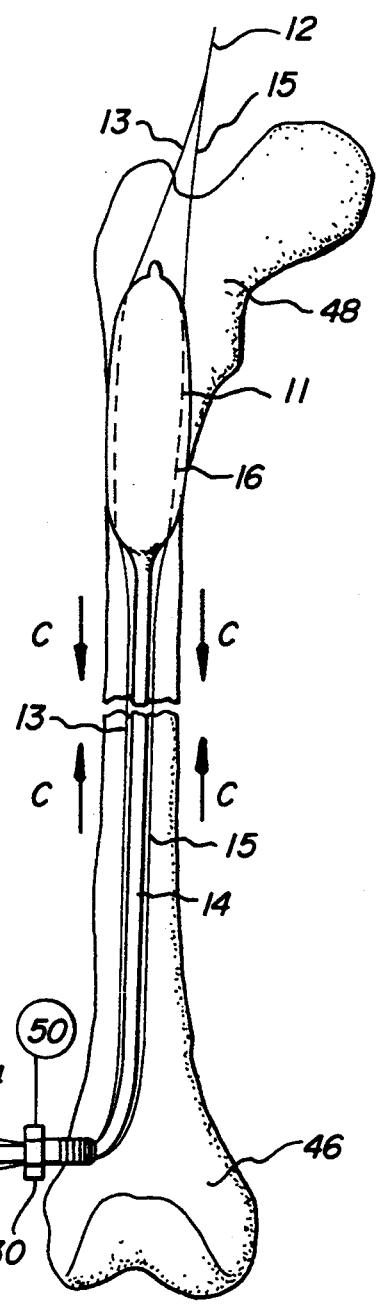
Fig. 3
Fig. 2

BALLOON COMPRESSOR FOR INTERNAL FIXATION OF BONE FRACTURES

BACKGROUND OF THE INVENTION

1. Related Cases

This is a continuation-in-part of U.S. patent application Ser. No. 08/130,434, filed Oct. 1, 1993.

2. Field of the Invention

The present invention is generally directed toward an apparatus for the internal fixation of fractures of tubular bones by compression.

3. Brief Description of the Background

Currently, fractured tubular bones are transfixed surgically by either metal plates and screws or intramedullary metal rods.

It is known that with internal fixation of fractures with plate and screw devices it is desirable to apply a compressive force across the fracture site. Bone is a viscoelastic material and support of structure and transmission of load is the mechanical function of bone. Bone is strongest in compression and weakest in tension. When a compressive force is applied across a fracture site it allows the fractured segments of bone to be placed in close proximity and the compressive force stimulates the bone in healing. If compression is applied at the fracture site, the intimate contact of the bone fragments restores the structural stability of the bone and allows the direct transfer of force from fragment to fragment rather than only through the implant. A compressive force applied directly at the fracture site hastens the healing of bone by encouraging the formation of new osteons which bridge the fracture line promoting a primary type of bone healing.

Some bone fracture realignment procedures involve insertion of a wire into the medullary canal which is then guided through the bone segments often in conjunction with a partially inserted nail for leverage. When the segments are aligned, the nail is fully inserted and the wire is withdrawn.

Metal intramedullary devices, which function as internal splints, have been used for many years to align fractures of tubular bones. These devices may take the form nails, U.S. Pat. No. 5,034,013; tubular members, U.S. Pat. No. 4,467,794; or a multiple pin device, U.S. Pat. No. 4,457,301. A steerable intramedullary fracture reduction device having an elongated shaft with a steerable tip pivotally mounted to the distal end of the shaft is shown by U.S. Pat. No. 5,002,543. In this patent a tip actuating apparatus near the proximal end of the shaft enables the operator to steer the tip and the shaft into successive segments of the fractured bone, even when the segments are transversely or rotationally displaced so that the segment can be aligned by the shaft. Metal compression devices which are used for fractures are shown by U.S. Pat. Nos. 4,275,717; 4,227,518; 3,779,239 and 3,760,802. The aforenoted metal compression devices are generally directed towards a threaded rod which is inserted within the medullary canal of a fractured tubular bone. The rod is provided with a distal end having an expandable spreadable sheath or fingers which expand upon rotation of the rod. The proximal end of the rod is located outside of the bone and is provided with a nut which holds the rod in place inside the bone thereby causing the fractured bone portions to be held together. U.S. Pat. No. 4,946,459 shows an intramedullary device for fixing and extending separated portions of a long bone within the body of a patient. The device has a tubular sleeve which is nailed to one end of the bone and an adjustment assembly with a moveable member which bears against an end of the nail. The moveable member can be moved from outside the patient to adjust the separation between the portions of the fractured bone.

The aforementioned prior art devices have metal fingers or sleeves which engage the walls of the medullary canal of the bone with deleterious effects.

The use of such prior art intramedullary devices involves the reaming of the medullary cavity which has the effect of destroying the inner lining of blood vessels. Furthermore the ends of long bones in children are also the growth center of the bones. Drilling or gouging through the ends causes damage and may stop or deform further growth.

Other prior art devices currently use dynamic compression plates and screw devices to apply compression across the fracture site. However, for insertion of this type of device, it is necessary to make a large surgical incision over the outer cortex of the bone directly at the fracture site. Placing this type of fixation device entails the disturbance of the soft tissues overlying the fracture site, disturbance of the fracture hematoma, and stripping the periosteium of bone which compromises the blood supply to the bone at the fracture site.

A flexible bladder device has been described by U.S. Pat. No. 4,313,434 to align fractures intramedullarly. However, this bladder device is designed to be placed directly at the fracture site to provide fixation. The bladder device was not designed for compression at the fracture site and when inflated at the fracture site actually promotes separation of the fracture fragments and has the opposite effect of the present balloon catheter compression device.

There is no known intramedullary device currently available that applies a compressive force at the fracture site in addition to aligning the fracture.

SUMMARY OF THE INVENTION

An improved method and apparatus for treatment of fractures of tubular bones relies on the principle of compressive force to align fractures of tubular bones and to promote and hasten the healing of such fractures. The intramedullary balloon of the balloon catheter is designed to be guided and transported through the medullary canal of the bone and placed either proximal or distal to the fracture site. The balloon when inflated with sterile saline solution is held securely in place in the medullary canal of the bone acting as an intramedullary anchor for the balloon catheter. It is the elastic property of the catheter that when tightened against the rigid immobile force of the anchoring balloon allows the fractured segments of the bone to align and come in intimate contact. With further tightening of the catheter a compressive force is applied across the fracture site.

It is an object of the invention to provide a fracture compression device which minimizes damage to the interior blood vessels and periosteum of the bone and allows the guide wire to be removed.

In the accompanying drawings, there is shown an illustrative embodiment of the invention from which these and other objectives, novel features and advantages will be readily apparent.

BRIEF DESCRIPTION OF THE DRAWINGS

FIG. 1 is a cross sectional schematic of the invention showing insertion of the inventive balloon catheter device into the bone;

FIG. 2 is a cross sectional schematic of the invention showing fixation of the balloon catheter in the medullary canal of the bone and compressive tightening of the fractured portions of the bone with the sensing and fluid transmission elements shown in block diagram; and FIG. 3 is a cross section of the inflated balloon with a fluted outer wall.

DETAILED DESCRIPTION OF THE INVENTION

A preferred embodiment and best mode of the invention is shown in FIGS. 1 and 2. The intramedullary balloon compression device 10 is used to treat fractures of tubular bones by applying intramedullary compression at the fracture site.

When a tubular bone 40 is fractured at a fracture site 41 the catheter device 10 can be inserted into the medullary canal 42 of the bone through a small incision either proximal or distal to the site of the fracture via a catheter introducer. A small aperture 44 is made in the outer cortex of the bone portion 46 with an introducing bone drill and drill bit or bone awl to access the medullary canal of the bone. Once the aperture 44 is created in the bone, the balloon catheter device 10 with lead wire 12 and double guide wires 13 and 15 or additional guide wires if such are needed is inserted into the medullar cavity of the bone by a catheter introducer 60. The balloon compression device 10 is preferably constructed of a plastic extruded material such as polyethylene, teflon, kevlar or other durable material is then guided by the guide wires 13 and 15 past the fracture site 41 into the other portion 48 of the fractured bone. The balloon catheter device 10 is formed with a plurality of lumens 11 along its length for guide wire insertion. Location of the lumens 11 are shown in phantom in FIG. 2. The guide wires may be removable from the balloon catheter or permanently incorporated in the catheter. The balloon 16 of the catheter device is inflated to its maximum diameter via the elastic catheter tube 14 with sterile saline solution by means of a syringe 18, associated feed tube 20 and a balloon pressure gauge monitor 22 as shown by respective block diagrams. It is envisioned that the shape of the balloon 16 can be modified in various forms, including smooth, fluted as shown in FIG. 3 or ridged outer walls for promoting endosteal blood supply at the site of the balloon insertion. The inflated balloon 16 is held securely in place by the positive pressure applied to the intramedullary walls of the bone. Once the balloon 16 is anchored in place past the fracture site 41, the attached catheter tube 14 can be tightened. The catheter tensioning device is provided with a calibrated force measuring device such as a strain gauge 50 to measure the compression force. The tightening of the catheter 14 with the fixed balloon 16 in place aligns the fracture and compresses the proximal and distal portions 46 and 48 of the fractured bone together. After alignment and compression of the fracture with the intramedullary balloon compression catheter, the catheter 14 is secured firmly to the bone 46 at it's insertion site 44 with a screw, post or peg type of fixation device 30. Thus, the balloon compression catheter can be incorporated into existing bone fixation technology such as an intramedullary rod, a fixation screw or plate, hip screw or total joint arthroplasty that uses a balloon catheter to enhance fixation to the bone. If desired the post 30 can be hollow and exteriorly threaded with the catheter tube 14 extending through the lumen 31 of the post 30 where the catheter tube 14 can be tied, clamped or affixed to a cross post mounted to the bone fixation post or strain gauge 50. The fixation post 30 and catheter 14 can be tightened, if necessary, to apply further compression at the fracture site. After the fracture heals, the balloon can be deflated and the balloon catheter and fixation post can be easily removed from the bone. If necessary, additional balloon catheters can be similarly positioned in place for fixation. The balloon compression catheter can be used independently for the intramedullary compression fixation of tubular bones or can be used as a supplement to metal intramedullary devices to apply compression across the fracture site.

The balloon catheter compression device 10 is inserted through a very small incision in the bone far away from the fracture site with a catheter introducer. The balloon 16 itself is transported through the medullary canal by the guide wires and is inflated away from the fracture site and in doing so does not compromise the extramedullary periosteal blood supply or the intramedullary blood supply at the fracture site. The device does not disturb the fracture hematoma which is essential for healing of the fracture. The compression force of the catheter allows the fractured fragments of bone to be aligned in close apposition promoting healing of the fracture similar to the prior art dynamic compression plate device without making an incision at the fracture site and without compromising the blood supply at the fracture site.

The intramedullary balloon compression catheter is designed specifically to apply a compressive force at the fracture site, to align the fractured bone and promote healing of the fracture.

Osteogenesis is promoted by compression across a fracture site and the intramedullary balloon compression catheter facilitates this in an intramedullary fashion.

In the foregoing description, the invention has been described with reference to a particular preferred embodiment, although it is to be understood that specific details shown are merely illustrative, and the invention may be carried out in other ways without departing from the true spirit and scope of the following claims:

What is claimed:

1. A method of setting a fractured bone by compression comprising the steps of:
   a) cutting an aperture into one portion of the fractured bone away from the site of the fracture allowing communication with the medullary canal of the bone;
   b) inserting a balloon catheter device and catheter guide wire means through the aperture cut in the bone into the medullar cavity of the bone;
   c) transporting the balloon catheter in the medullary canal of the bone past the fracture site by use of the catheter guide wire means to a point distal from the fractured site;
   d) inflating the balloon of the balloon catheter device to its maximum diameter so that the balloon catheter device is held securely in place by the positive pressure of the balloon applied to the intramedullary walls of the bone; and e) tensioning the attached catheter with the fixed balloon in place by securing the catheter under tension to holding means to align the fracture and compress the proximal and distal portions of the fractured bone together.

2. The method of claim 1 including the step of; f) securing the catheter firmly to the bone at the insertion site with a fastener device.

3. The method of claim 2 wherein said securing step uses a screw as the securing device.

4. The method of claim 2 wherein said securing step uses a bolt as the securing device.

5. The method of claim 2 wherein said securing step uses a post as the securing device.

6. The method of claim 1 wherein said cutting step uses an bone awe to cut the aperture.

7. The method of claim 1 wherein said cutting step uses a bone drill to cut the aperture.

8. An assembly for setting a fractured bone comprising a balloon catheter with tubing, said balloon catheter defining an inflation section which inflates when said balloon catheter is pressurized and a plurality of throughgoing lumens, a guide wire mounted in each of said lumens, said inflation section being inflated in a fractured bone portion to fixedly engage said bone segment and anchor means adapted mounted in another fractured bone portion distal from said fractured bone portion, said anchor means being secured to said catheter tubing to hold said balloon catheter in a tensioned condition which provides compression on the fracture site of fractured bone portions.

9. The assembly of claim 8 including a calibrated force measuring device secured to said tubing to measure the compression force on said balloon catheter.

10. The assembly of claim 8 including a pressure monitoring means connected to said balloon catheter to measure the pressure of the inflated balloon of said balloon catheter.

11. The assembly of claim 8 wherein said balloon catheter is a plastic extruded material.

12. The assembly of claim 11 wherein said catheter tubing is elastic and constructed of plastic.

13. The assembly of claim 8 wherein said holding means is a hollow post with holding means.

14. The assembly of claim 8 wherein said balloon portion of said balloon catheter has an outer wall which is ridged.

15. The assembly of claim 8 wherein said balloon portion of said balloon catheter has an outer wall which is smooth.

16. The assembly of claim 8 wherein said balloon portion of said balloon catheter has an outer wall which is fluted.

17. The assembly of claim 8 wherein said balloon catheter defines two lumens.

18. The assembly of claim 8 wherein said balloon catheter defines at a least three lumens.

19. The assembly of claim 8 wherein said guide wires are removably mounted in said lumens.

20. The assembly of claim 8 wherein said guide wires are secured in said lumens.

* * * * *